United States Patent [19]

Eibl

[11] Patent Number: 5,049,552

[45] Date of Patent: Sep. 17, 1991

[54] COMPOSITIONS CONTAINING HEXADECYLPHOSPHOCHOLINE AND USE THEREOF

[75] Inventor: Hansjörg Eibl, Bovenden, Fed. Rep. of Germany

[73] Assignee: Max-Planck-Gesellschaft Zur Foerderung Der Wissenschaften E. V., Goettingen, Fed. Rep. of Germany

[21] Appl. No.: 316,413

[22] Filed: Feb. 27, 1989

Related U.S. Application Data

[62] Division of Ser. No. 97,960, filed as PCT EP86/00705 on Dec. 4, 1986, published as WO87/03480 on Jun. 18, 1987, Pat. No. 4,837,023.

[30] Foreign Application Priority Data

Dec. 4, 1985 [DE] Fed. Rep. of Germany ....... 3542893
Feb. 28, 1986 [DE] Fed. Rep. of Germany ....... 3606631

[51] Int. Cl.$^5$ .......................................... H61K 31/685
[52] U.S. Cl. ..................................................... 514/77
[58] Field of Search ........................................ 514/77

[56] References Cited

PUBLICATIONS

Chemical Abstracts 101:23066g (1984).
Chemical Abstracts 108:48864k (1988).
Chemical Abstracts 108:87670p (1988).
Chemical Abstracts 108:179609d (1988).

*Primary Examiner*—Jerome D. Goldberg
*Attorney, Agent, or Firm*—Felfe & Lynch

[57] ABSTRACT

The invention relates to compositions containing hexadecylphosphocholine and the use of these in treating various cancers.

17 Claims, No Drawings

COMPOSITIONS CONTAINING HEXADECYLPHOSPHOCHOLINE AND USE THEREOF

This application is a divisional of Ser. No. 097,960, filed as PCT EP86/00705 on Dec. 4, 1986, published as WO87/03480 on Jun. 19, 1987 now U.S. Pat. No. 4,837,023.

BACKGROUND OF THE INVENTION

Hexadecylphosphocholine is a known substance. In Pharmazie 37, 1982, pages 706-707, a lysing and fusogenic action is stated herefor. It has now been found that this compound also possesses an excellent anti-tumor action and, in comparison with homologous compounds, which are described in European Application 108 565, is characterized by the following surprising properties: whereas similar compounds with a shorter alkyl radical, such as for example tetradecylphosphocholine, show practically no anti-tumor action (for example, in vitro in the L1210 colony experiment or in vivo on the autochtanous methylnitrosourea-induced mammary carcinoma of the rat), those with a longer alkyl radical, such as for example octadecylphosphocholine, are admittedly anti-tumor effective but, at the same time, far too toxic and, therefore, not usable as medicaments. Thus, for example, in the case of a determination of the subacute toxicity during a treatment of 5 weeks at an anti-tumor effective daily dose of 77 $\mu$mole/kg. rat orally, there was obtained an extremely high mortality which was 80% of all animals. Therefore, in spite of an anti-tumor action, the median survival time in comparison with the control was shortened by 72% in the case of octadecylphosphocholine-treated animals. In comparison thereto, in the case of hexadecylphosphocholine-treated animals, the mortality was lower by a half and, as a result of the absence of a chronic toxicity, it resulted in a highly significant increase of the median survival time of 26% in comparison with the controls.

Thus, within the homologous alkyl compounds, hexadecylphosphocholine occupies a surprising special position in that only hexadecylphosphocholine possesses a practically useful good anti-tumor action. Homologues with shorter alkyl radicals possess no or a much too low anti-tumor action. Homologues with longer alkyl radicals are admittedly effective against tumors but, at the same time, are much too toxic. Therefore, only hexadecylphosphocholine displays a sufficient anti-tumor action in non-toxic doses.

The invention concerns medicaments which contain hexadecylphosphocholine as active material and are especially suitable for the treatment of tumors sensitive to treatment with hexadecylphosphocholine.

Such medicaments possess an outstanding cytotoxic effectiveness which was demonstrated not only in vivo on chemically-induced mammary carcinoma of the rat but also in vitro on leukaemia cells in the cell culture. Furthermore, in a clinical pilot study in the case of female patients with mammary carcinomas, skin metastases were completely healed in the case of topical use.

It is known that hitherto no medicament for the treatment of tumors, especially of malignant tumors, was available which was satisfactory in all respects. Thus, for example, for the topical treatment of skin metastases in patients with metastasizing tumors, at present only 5-fluorouracil is available. Further developments of other cytostatics have hitherto not progressed to clinical maturity for this manner of administration. On the other hand, from a clinical point of view, such a concept of palliative therapeutic use is especially desirable since alternative concepts of treatment, such as surgical measures, radiation therapy and systemic chemotherapy, constitute comparatively aggressive therapy modalities. Furthermore, a considerable number of patients are available as potential treatment candidates for such a topical treatment. Thus, e.g. the proportion of mammary carcinoma patients who display a skin attack amounts to about 25 to 35%.

The prerequisite for topical treatment on the part of the active material to be used are compatibility to the skin, cytotoxic effectiveness against tumour cells and sufficiently deep penetration.

OBJECT OF THE INVENTION

Therefore, the object of the invention is, in the first place, to provide a medicament which is suitable for the topical treatment of tumors sensitive to treatment with hexadecylphosphocholine. A further object of the invention is, in addition, also to provide, in general, a medicament usable in other forms of administration which combines a good effectiveness against tumors sensitive to treatment with hexadecylphosphocholine with low toxicity and is, therefore, generally usable in tumor therapy.

DESCRIPTION OF THE INVENTION

According to the invention, these objects are solved by a medicament which is characterized in that it contains hexadecylphosphocholine as active material.

Especially for topical administration but also for the preparation as medicaments for other modes of administration, it has proved to be especially advantageous to use the hexadecylphosphocholine together with at least one alkylglycerol with 3 to 12 carbon atoms in the alkyl radical which can be present attached in the form of an ether group to one of the primary or secondary OH groups of the glycerol. Such alkylglycerols increase or improve the action of the hexadecylphosphocholine synergistically. There are hereby preferably used alkylglycerols with 3 to 9 C-atoms alone or as mixture.

Therefore, a synergistically-acting medicament which contains
a) hexadecylphosphocholine and
b) an alkyl glycerol of the general formula I

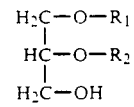

in which one of the radicals $R_1$ and $R_2$ signifies an alkyl group with 3 to 12 C-atoms and the other radical an H-atom, as well as possibly further usual pharmacological additive and diluent materials, possesses especially favorable actions.

Such a mixture is, in the following, also called a cascade.

The content of hexadecylphosphocholine in mg./ml. of cascade is indicated by a subsequent index in such a manner that, for example, a cascade mixture which contains 5 mg./ml. of hexadecylphosphocholine is described as cascade$_5$, a mixture with 200 mg. of hexadecylphosphocholine per ml. of cascade as cascade$_{200}$.

The preparation of alkylglycerols is known, for example, from DE-OS 33 43 530.8.

Alkylglycerol-water mixtures which contain, for example, nonylglycerol, octylglycerol, hexylglycerol, pentylglycerol, propylglycerol and ethylglycerol, are preferred. Such aqueous mixtures preferably contain 3 of the said glycerol ethers, namely, a lower one (ethyl, propyl), a medium one (pentyl, hexyl) and a higher one (nonyl, octyl), whereby the amount by weight of the lower ether is about as great as the sum of amounts by weight of the two other glycerol ethers. The amount of water is about equal to the amount of the lower glycerol ether and amounts, for example, to half of the total amount of glycerol ethers present. Examples of such glycerol ether-water mixtures are set out in the following:

|  | water | glycerol propyl ether | glycerol hexyl ether | glycerol nonyl ether |
|---|---|---|---|---|
| parts by weight | 2 | 2 | 1 | 1 |

|  | water | glycerol ethyl ether | glycerol pentyl ether | glycerol octyl ether |
|---|---|---|---|---|
| parts by weight | 2 | 2 | 1 | 1 |

The medicaments according to the invention are suitable to a special degree for topical administration. In order to treat skin tumors or skin metastases sensitive to treatment with hexadecylphosphocholine with this medicament, the skin regions in question are rubbed in two to three times daily with cascade$_5$ to cascade$_{200}$. Harmful side effects have hitherto not been observed, not even in the case of patients who have been treated over a period of time of 3 months. The remission of the skin metastases is accompanied by a normalization of the skin, as could clearly be demonstrated by tissue sections. Several patients with skin metastases were treated in this way and a complete disappearance of the mammary carcinoma skin metastases hereby observed.

The topical treatment with the preferred agent according to the invention in the formulation cascade$_5$ to cascade$_{200}$ can also be used for the treatment of internal tumors or metastases by rubbing into large areas of the skin. Therapeutically effective blood levels are hereby achieved by absorption through the skin. An advantage of this mode of administration lies in the fact that the preparations cascade$_5$ to cascade$_{200}$ are tolerated by the skin without problems.

This preferred type of preparation of the medicament according to the invention in the form of solutions of cascade$_5$ to cascade$_{200}$ is also well suited for the preparation of suppositories for rectal insertion. Internal tumors or metastases sensitive to treatment with hexadecylphosphocholine can also be readily treated in this way.

Another form of use of the medicaments according to the invention consists in the instillation into preformed body cavities. This mode of administration is especially suitable for pleural carcinoses, malignant ascites, malignant pericardial discharges and bladder carcinomas. In this case, the hexadecylphosphocholine is used either alone or in combination with usual carrier and dilution agents, especially also with cascades.

For systemic administration, there comes into consideration, for example, oral or intravenous administration.

For oral administration, hexadecylphosphocholine is used, for example, in the form of a potable solution. As carriers there are suitable, for example, milk, cocoa, fruit juice or drinking water. The preparation of such a potable solution takes place, for example, by dilution of a concentrated alcoholic solution of hexadecylphosphocholine with water or another of the previously mentioned agents. In the case of rats, daily doses of 20, 40 and 60 mg./kg. body weight of hexadecylphosphocholine led to a complete remission of chemically induced mammary carcinomas. Hexadecylphosphocholine hereby proved to be better effective and better compatible than, for example 1-octadecyl-2-methyl-rac-glycero-3-phosphocholine. In the case of the tumor model used for these experiments, it is a question of a so-called hard model. This means that findings obtained with this model can also be transmitted to the human situation.

For the intravenous administration via the intravenous infusion therapy, the hexadecylphosphocholine is expediently used in physiological common salt solution. Other infusion solutions can hereby also be used. The dosage on humans for such solutions is, for example, 1–10 mg./kg. of body weight.

Finally, several forms of administration of the medicament according to the invention can be used combined, whereby the especial topic compatibility has the result that, on the one hand, a rubbing in of the skin can be combined with one of the other forms of administration.

A further carrier mixture for hexadecylphosphocholine which has proved to be especially useful consists of a mixture of about 4 parts by weight of water, 4 parts by weight of propylglycerol and 2 parts by weight of each of hexylglycerol and nonylglycerol.

The topical use of the medicament according to the invention in the especially preferred form of preparation of cascade$_5$ to cascade$_{200}$ over a period of time of several months shows that the local toxicity is limited to an increased desquamation of the skin, similarly to the local use of acetylsalicylic acid.

Thus, the invention makes available a new medicament for the treatment of tumors sensitive to treatment with hexadecylphosphocholine and hereby provides not only a further anti-tumor agent but also provides, for the first time, an agent which has also been shown to be effective in the case of topical administration in clinical experiments. New possibilities for the treatment of tumor patients are hereby opened up.

For the preparation of appropriate medicaments, hexadecylphosphocholine is worked up with conventional pharmaceutical carrier materials and/or dilution agents or other adjuvant materials to pharmaceutical compositions or is brought into a therapeutically usable form. This takes place, for example, in that the hexadecylphosphocholine is mixed or homogenized together with usual carrier and/or dilution or adjuvant materials at temperatures between 20° and 120° C., preferably 30°–100° C., the so obtained mixture is, for the preparation of compositions which contain 5 to 2000 mg., preferably 10 to 500 mg. and especially 30 to 400 mg. hexadecylphosphocholine, poured into hollow cells of appropriate size or filled into capsules of appropriate size or granulated and then pressed into tablets, possibly with the addition of further usual adjuvant materials.

For example, in that one mixes hexadecylphosphocholine with one or more of the following materials: starch, cellulose, lactose, formalin-casein, modified starch, magnesium stearate, calcium hydrogen phosphate, highly dispersed silicic acid, talc, phenoxyethanol, granulates the mixture obtained, possibly with an aqueous solution which, as component, contains at least gelatine, starch, polyvinylpyrrolidone, vinylpyrolidonevinyl acetate co-polymer and/or polyoxyethylsorbitan monooleate, homogenizes the granulate possibly with one or more of the above-mentioned adjuvant materials and presses this mixture to tablets or fills into capsules, whereby such tablets or capsules in each case contain 5 to 2000 mg. hexadecylphosphocholine, or that, after the addition of soya lecithin, as well as possibly of 0.1–0.5 parts by weight of phenoxyethanol (referred to one part by weight of hexadecylphosphocholine), suspends hexadecylphosphocholine at temperatures between 33°–37° C. in molten hard fat and homogenizes and subsequently pours the mixture into hollow cells, whereby the dosage unit contains 5 to 2000 mg. hexadecylphosphocholine, as well as possibly 0.1–0.5 parts by weight of phenoxyethanol (referred to one part by weight of hexadecylphosphocholine), or in that one homogenizes hexadecylphosphocholine at a temperature between 50° C. and 120° C., preferably 50° C. to 100° C., possibly in the presence of one or more emulsifiers and/or 0.1–0.5 parts by weight of phenoxyethanol (referred to one part by weight of hexadecylphosphocholine) with at least one of the following materials: paraffin, vaseline, aliphatic alcohol with 12 to 25 C-atoms, aliphatic monocarboxylic acid with 15 to 20 C-atoms, sorbitan monopalmitate, polyoxythylenepolyol fatty acid ester, and emulsifies the mixture obtained between 50° and 120° C. with water, possibly with the addition of a polyhydroxy lower aliphatic alcohol and/or phenoxyethanol; or in that one dissolves hexadecylphosphocholine in water or vegetable oil, possibly in the presence of 0.1–0.5 parts by weight of phenoxyethanol (referred to one part by weight of hexadecylphosphocholine), as well as possibly in the presence of an emulsifier, at temperatures between 30°–100° C., and possibly makes up the so obtained solution with so much water or vegetable oil that the final solution contains 0.05 to 10 percent by weight, preferably 0.1 to 5 percent by weight, of hexadecylphosphocholine.

As emulsifiers, there come into question, for example: non-ionic emulsifiers, as well as ionic emulsifiers. In the case of non-ionic emulsifiers, it is a question of, for example, triglyceride mixtures of saturated vegetable fatty acids with $C_8$, $C_{10}$ and $C_{12}$ or of emulsifiers based on polyaddition products of ethylene oxide, such as, for example, alkyl- and acyl-substituted polyaddition products of ethylene oxide, polyethyleneglycol fatty acid esters, reaction products of ethylene oxide with castor oil, esters of hydrogenated castor oil fatty acids with oxyethylated glycerol. Furthermore, it can be a question of emulsifiers based on fatty acid amides or fatty acid condensation products with hydrophilic groups. As ionic emulsifiers, there come into question, for example, emulsifiers based on fatty acid monoesters of glycerol or of other polyhydroxy alcohols (Lunacera alba).

If, in the case of the above-given preparation of the medicaments, the hexadecylphosphocholine is used in the presence of a glycerol ether of formula I or of a mixture of such glycerol ethers of formula I, there is observed a synergistic action increase of the antitumor action.

For this purpose, the hexadecylphosphocholine is used with 1 to 30, preferably 2 to 20 parts by weight (referred in each case to one part by weight of hexadecylphosphocholine) of at least one glycerol ether of formula I or a mixture of such glycerol ethers, as well as possibly 0.5–30, preferably 1–20 parts by weight of water (also referred to one part by weight of hexadecylphosphocholine). This mixing with the glycerol ethers can take place initially in the preparation of the appropriate medicaments but possibly also at a later stage of preparation.

Hexadecylphosphocholine shows, for example, a good action on 7,12-dimethylbenzanthracene-induced mammary carcinoma of the rat; as well as on methylnitrosourea-induced mammary carcinoma of the rat.

For example, in the case of the above-mentioned experimental method, at a dose of 10 mg./kg. body weight of rat, there is achieved a cessation of growth of the tumors, at higher doses also a complete disappearance of the growths.

The lowest already effective dose in the above-mentioned animal experiment is, for example
5 mg./kg. orally
5 mg./kg. intravenously.

As general dose range for the action (animal experiment as above), there comes into question, for example:
5–50 mg./kg. orally, especially 15–32 mg./kg.
5–50 mg./kg. intravenously, especially 15–32 mg./kg.

The direction of action of the compounds according to the invention is comparable with the action of the known medicament active material TAMOXIFEN but, in this regard, there exist the following differences: The action is stronger and of longer duration than that of TAMOXIFEN.

Indications for which the compounds of the invention come into consideration: breast cancer and other kinds of human cancer sensitive to treatment with hexadecylphosphocholine.

The pharmaceutical compositions contain, in general, between 5–2000 mg., for example 10–400 mg. of hexadecylphosphocholine.

The administration can take place, for example, in the form of tablets, capsules, pills, dragees, cones, salves, gels, creams, powders, dusting powders, aerosols or in liquid form. As liquid forms of use, there come into question, for example: oily or alcoholic or aqueous solutions, as well as suspensions and emulsions. Preferred forms of use are tablets which contain between 0.1% to 5% of active substance.

The individual dose of hexadecylphosphocholine can, for example, lie
a) in the case of oral medicinal forms between 5–100 mg./kg. body weight, preferably 15–50 mg./kg. body weight,
b) in the case of parenteral medicinal forms (for example intravenous, intramuscular) between 5–100 mg./kg. body weight,
c) in the case of medicinal forms for local administration to the skin or mucous membranes (for example in the form of solutions, lotions, emulsions, salves and so forth) between 50–2000 mg., preferably 80–1500 mg.

For example, 1 tablet with a content of 40–400 mg. of active substance can be recommended 3 times daily or, for example, in the case of intravenous injection, 1–5 times daily an ampule of 1–5 ml. content with 50–250 mg. of substance. In the case of oral administration, the minimum daily dose lies, for example, at 120 mg.; the maximum daily dose in the case of oral administration is not to lie above 100 mg./kg.

The acute toxicity of hexadecylphosphocholine in the mouse (expressed by the LD 50 mg./kg.; method according to Miller and Tainter, Proc. Soc., Exper. Biol. a. Med. 57 (1944) 261) lies, for example, in the case of oral administration, between 200 and 450 mg./kg. body weight.

The medicaments can be used in human medicine, in veterinary medicine, as well as in agriculture, alone or in admixture with other pharmaceutically active materials.

The invention is explained by the following Examples.

EXAMPLE 1

Preparation of hexadecylphosphocholine.H$_2$O a) Hexadecylphosphoethanolamine (phosphorylation, ring closure and ring opening)

Hexadecanol (1 mole, 243 g.) and triethylamine (1.8 mole, 180 g.) are dissolved in 1.5 l. THF (tetrahydrofuran) and added dropwise to a vigorously stirred solution of phosphorus oxychloride (1.2 mole, 184 g.) in 120 ml. THF in such a manner that the temperature in the reaction vessel (three-necked, 5.l., with dropping funnel, thermometer and stirrer) does not exceed 10° C. For the acceleration of the procedure, the reaction vessel is cooled with an ice-salt mixture. Immediately after the dropping in, the reaction is terminated (detection via TLC in ether: Rf values of 0.8 for the starting product, of 0.0 for the reaction product after hydrolysis with water).

One removes the ice bath and drops into the reaction mixture, with vigorous stirring, a solution of ethanolamine (1.5 mole, 92 g.) and triethylamine (1.8 mole, 180 g.) in 1.1 dioxan in such a manner that the temperature in the reaction vessel increases to 65° to 70° C. The ring formation is then concluded (detection by TLC in ether: Rf value of 0.2). One filters off from precipitated triethylamine hydrochloride while still warm and mixes the filtrate at 40° to 50° C. with 1.5 l. 2N formic acid. After 15 minutes, the ring opening is concluded (detection of TLC in ether: Rf value 0.0; TLC in chloroform/methanol/acetic acid/water 100:60:20:5 in vol.: Rf value 0.8). One cools to −20° C., filters off the precipitate which consists substantially of pure hexadecylphosphoethanolamine. In the case of slight impurities, a chromatographic purification is carried out (see

EXAMPLE 2). MICROANALYSIS (M. W. 365.50)

calc. (%): C 59.15; H 11.03; N 3.83; P 8.48.
found (%): 59.01; 10.95; 3.79; 8.31.

b) (Methylation of 1)

The crystals obtained according to Example 1 are, without further purification, taken up in 1.2 l. 2-propanol and 0.4 l. dichloromethane. One mixes the suspension of the crystals, with vigorous stirring, with potassium carbonate (4 mole, 560 g.) in 1.1. of water. The two-phase reaction mixture is mixed dropwise and while stirring with dimethyl sulphate (4 mole, 500 g.) in such a manner that the temperature does not exceed 40° C. The reaction is ended 60 minutes after the dropping in (detection by TLC in chloroform/methanol/ 25% ammonia 50:50:5 in vol.; Rf value 0.3). After phase separation at 20° C., the upper phase contains the product. One removes the solvent on a rotary evaporator under vacuum and chromatographs the viscous residue on silica gel (Merck Art. 7733, silica gel 60, grain size 0.2 to 0.5 mm.).

Chromatograph

Silica gel, 2 kg.,are mixed with chloroform/methanol/25% ammonia (200/15/1 in vol.) and filled into a chromatography column. One dissolves the viscous oil in 800 ml. of the above solvent mixture and applies the crude product to the column (insoluble components are previously filtered off). One elutes with elution agents of increasing polarity until the impurities are washed out. The product is finally eluted with chloroform/methanol/25% ammonia (50/50/5 in vol.). The combined eluates are rotary evaporated and the residual water removed with toluene. The residue is taken up in 600 ml. dichloromethane and mixed with 4 l. of acetone. The crystals which separate out at −20° C. are washed with cold acetone, then with pentane and dried in a vacuum. The yield of pure hexadecylphosphocholine amounts to 250 g. (about 70% referred to hexadecylglycerol).

Microanalysis (M.W. 407.58).
calc. (%): C 59.27; H 11.37; N 3.29; P 7.28.
found (%): 58.98; 11.31; 3.24; 7.11.

Examples for pharmaceutical compositions

EXAMPLE FOR A SOLUTION 25 g. 1-n-propoxy-2,3-propanediol, 12.5 g. 1-n-hexyloxy-2,3-propanediol, 12.5 g. 1-n-nonyloxy-2,3-propanediol, 44 g. water and 1 g. phenoxyethanol are mixed and 5 g. hexadecylphosphocholine dissolved in this mixture. The solution is freed from visible particles by filtration over a suitable filter.

1 g. of solution contains 50 mg. hexadecylphosphocholine.

EXAMPLE FOR A SALVE 5 g. of substance hexadecylphosphocholine are suspended in 35 g. very viscous paraffin, 30 g. emulsifying cetyl stearyl alcohol and 30 g. white vaseline are added thereto and melted. This melt is stirred until cold. A homogeneous active material distribution is achieved by working up of the cooled melt by means of a suitable homogenisation apparatus (for example a three-roll mill).

1 g. of the hydrophilic salt contains 50 mg. hexadecylphosphocholine.

EXAMPLE FOR AN EMULSION 11.83 g. 1-n-propyloxy-2,3-propanediol, 5.91 g. 1-n-hexyloxy-2,3-propanediol, 5.91 g. 1-n-nonyloxy-2,3-propanediol, 20.35 g. water and 1.0 g. phenoxyethanol are mixed and 5 g. hexadecylphosphocholine dissolved in this mixture. On a waterbath, 30 g. white vaseline, 15 g. cetyl alcohol and 5 g. sorbitan monopalmitate are melted, heated to 70° C. and the active material solution, also heated to 70° C., emulsified in the fat phase with the help of a high-speed dispersion apparatus. Subsequently, the cream is cooled to 30° C. while stirring.

1 g. of water-in-oil cream contains 50 mg. hexadecylphosphocholine.

EXAMPLE FOR CAPSULES 1.25 kg. hexadecylphosphocholine are dissolved in 5 kg. chloroform and 1.25 kg. Aerosil suspended in this solution. Subsequently, the solvent is stripped off in a vacuum. The dry mass is passed through a 1 mm. sieve and again dried in a vacuum at 30° C. in order to remove last residues of solvent. This granulate is filled in known manner on a suitable capsuling machine into hard gelatin capsules of the size 00 in an amount of 500 mg.

One capsule contains 250 mg. hexadecylphosphocholine.

EXAMPLE FOR A LYOPHILIZATE

In 3 liters of water for injection purposes are dissolved, with nitrogen gassing, 500 g. mannitol, 50 g. hexadecylphosphocholine are dispersed with the help of a high-speed homogenizing apparatus and made up to 4 liters with water for injection purposes. This milky dispersion is converted into a slightly opalescing, colloid-disperse system by ultrasonic treatment or with the help of a slot homogenizer.

Under aseptic conditions, it is now sterile filtered over a membrane filter of 0.22 μm. pore width and filled in 40 ml. amounts into 100 ml. injection bottles with nitrogen gassing. One provides the bottles with freeze-drying stoppers and lyophilizes in a suitable plant. After the drying, it is gassed with sterile, dry nitrogen and the bottles closed in the plant. The stoppers are secured with a flanged cap.

For intravenous use, the lyophilizate is reconstituted in 100 ml. water for injection purposes. 1 Bottle contains 500 mg. hexadecylphosphocholine.

I claim:

1. The method of treating a cancer sensitive to treatment with hexadecylphosphocholine, which consists of administering to a patient afflicted with said cancer a therapeutically effective anti-cancer amount of hexadecylphosphocholine.

2. Method of claim 1, wherein said cancer is an internal tumor or internal metastasis, a plural carcinosis, a malignant ascites, a pericardial carcinoma, a mammary cancer or a bladder carcinoma.

3. Method of claim 1, wherein said hexadecylphosphocholine is administered in an oral formulation.

4. Method of claim 3, wherein said hexadecylphosphocholine is administered in an amount ranging from 5 mg to 100 mg of hexadecylphosphocholine per kilogram of body weight of said patient.

5. Method of claim 1, wherein said hexadecylphosphocholine is administered in connection with starch, cellulose, lactose, formalin-casein, modified starch, magnesium stearate, calcium hydrogen phosphate, highly dispersed silicic acid, talc, phenoxyethanol, gelatin, polyvinylpyrrolidone, vinylpyrrolidone vinylacetate copolymer or polyoxyethylsorbitan monooleate or mixtures thereof 6. Method of claim 5, wherein said hexadecylphosphocholine is administered in the form of a tablet or capsule.

7. Method of claim 5, wherein said hexadecylphosphocholine is administered in dose ranging from 5 mg to 2000 mg.

8. Method of claim 1, wherein said hexadecylphosphocholine is administered in connection with a nonionic emulsifier or an ionic emulsifier.

9. The method of claim 1, wherein said hexadecylphosphocholine is administered in the form of a mixture consisting essentially of 5 to 200 mg of hexadecylphosphocholine and a pharmaceutically acceptable carrier.

10. Method of claim 9 wherein said mixture contains water.

11. Method of claim 9, wherein said mixture is administered in the form of a composition suitable for local application.

12. Method of claim 11, wherein said mixture is administered two or three times per day.

13. Method of claim 11, wherein said mixture is administered to a skin tumor or skin metastasis.

14. Method of claim 13, wherein said skin metastasis is a mammary carcinoma.

15. Method of claim 9, wherein said mixture is administered in the form of a solution, a suppository, an oral medicament, a parenteral medicament or a medicament suitable for local administration.

16. Method of claim 15, wherein said hexadecylphosphocholine is administered in a parenteral medicament which further comprises a physiologically acceptable salt solution in an amount ranging from 5 to 100 mg of hexadecylphosphocholine per kilogram of body weight of said patient.

17. Method of claim 15, wherein said hexadecylphosphocholine is administered in a medicament suitable for local administration which contains from 50 mg to 2000 mg of hexadecylphosphocholine.

* * * * *

UNITED STATES PATENT AND TRADEMARK OFFICE
CERTIFICATE OF CORRECTION

PATENT NO. : 5,049,552

DATED : September 17, 1991

INVENTOR(S) : Hansjörg Eibl

It is certified that error appears in the above-identified patent and that said Letters Patent is hereby corrected as shown below:

Column 1, line 22, "autochtanous" should read --autochthanous--.

Column 3, chart, "2  2  1  1" (both instances) should read --2 : 2 : 1 : 1--.

Column 10, line 4, claim 5, after "thereof" insert --.--.

Signed and Sealed this

Sixteenth Day of March, 1993

Attest:

STEPHEN G. KUNIN

Attesting Officer

Acting Commissioner of Patents and Trademarks